(12) United States Patent
Giambattista et al.

(10) Patent No.: US 10,322,244 B2
(45) Date of Patent: Jun. 18, 2019

(54) MEDICAMENT DELIVERY DEVICE

(71) Applicant: SHL GROUP AB, Nacka Strand (SE)

(72) Inventors: Lucio Giambattista, East Hannover, NJ (US); Antonio Bendek, Vernon, NJ (US); Ling-Hsiang Chao, Taipei (TW)

(73) Assignee: SHL GROUP AB, Nacka Strand (SE)

( * ) Notice: Subject to any disclaimer, the term of this patent is extended or adjusted under 35 U.S.C. 154(b) by 0 days.

(21) Appl. No.: 15/673,207

(22) Filed: Aug. 9, 2017

(65) Prior Publication Data

US 2017/0340831 A1  Nov. 30, 2017

Related U.S. Application Data

(63) Continuation-in-part of application No. 14/948,641, filed on Nov. 23, 2015, now Pat. No. 9,744,308, (Continued)

(30) Foreign Application Priority Data

Dec. 15, 2009 (SE) .................................. 0950958-9

(51) Int. Cl.
| | | |
|---|---|---|
| *A61M 5/00* | (2006.01) | |
| *A61M 5/178* | (2006.01) | |
| *A61M 5/315* | (2006.01) | |
| *A61M 5/31* | (2006.01) | |
| *A61M 5/24* | (2006.01) | |

(52) U.S. Cl.
CPC ...... *A61M 5/31551* (2013.01); *A61M 5/3158* (2013.01); *A61M 5/31553* (2013.01); *A61M 5/24* (2013.01); *A61M 5/31541* (2013.01); *A61M 5/31561* (2013.01); *A61M 5/31595* (2013.01); *A61M 2005/2407* (2013.01); (Continued)

(58) Field of Classification Search
CPC ...... A61M 2005/3126; A61M 5/31551; A61M 5/31553; A61M 5/3158; A61M 2205/581; A61M 2205/582; A61M 5/31541
See application file for complete search history.

(56) References Cited

U.S. PATENT DOCUMENTS

| | | |
|---|---|---|
| 5,921,966 A | 7/1999 | Bendek et al. |
| 6,042,571 A | 3/2000 | Hjertman et al. |

(Continued)

FOREIGN PATENT DOCUMENTS

| | | |
|---|---|---|
| DE | 102004063652 | 7/2006 |
| WO | 01/95959 | 12/2001 |

(Continued)

OTHER PUBLICATIONS

International Search Report and Written Opinion for International Patent App. No. PCT/US2010/060022.

*Primary Examiner* — Rebecca E Eisenberg
(74) *Attorney, Agent, or Firm* — McDonnell Boehnen Hulbert & Berghoff LLP

(57) ABSTRACT

A dose setting mechanism for a medicament delivery device is presented having a locking assembly that reliably and consistently unlocks a dose injection button and concurrently a lead screw when the dose setting mechanism is transitioned from a non-activated state to an activated state. This locking assembly uses a rotating plate having a locking protrusion that engages a radial projecting tab on a rotationally fixed plunger rod nut. An alignment member is also presented that prevents rotational drift of a dosing member.

20 Claims, 13 Drawing Sheets

Related U.S. Application Data which is a continuation of application No. 14/449,671, filed on Aug. 1, 2014, now Pat. No. 9,744,307, which is a continuation of application No. 13/896,639, filed on May 17, 2013, now Pat. No. 8,827,962, which is a continuation of application No. 13/203,040, filed as application No. PCT/US2010/060022 on Dec. 13, 2010, now Pat. No. 8,491,536.

(52) U.S. Cl.
CPC .............. *A61M 2005/3126* (2013.01); *A61M 2205/581* (2013.01); *A61M 2205/582* (2013.01)

(56) References Cited

U.S. PATENT DOCUMENTS

| | | |
|---|---|---|
| 6,221,053 B1 | 4/2001 | Walters et al. |
| 6,277,099 B1 | 8/2001 | Strowe et al. |
| 2005/0165363 A1 | 7/2005 | Judson et al. |
| 2008/0114305 A1 | 5/2008 | Gerondale |
| 2009/0275914 A1 | 11/2009 | Harms et al. |
| 2009/0275916 A1 | 11/2009 | Harms et al. |
| 2011/0034881 A1 | 2/2011 | Bartha |
| 2011/0306947 A1 | 12/2011 | Boyd et al. |
| 2012/0283648 A1 | 11/2012 | Veasey et al. |
| 2012/0302964 A1 | 11/2012 | MacDonald et al. |

FOREIGN PATENT DOCUMENTS

| | | |
|---|---|---|
| WO | 03/080160 | 10/2003 |
| WO | 2008/101829 | 8/2008 |

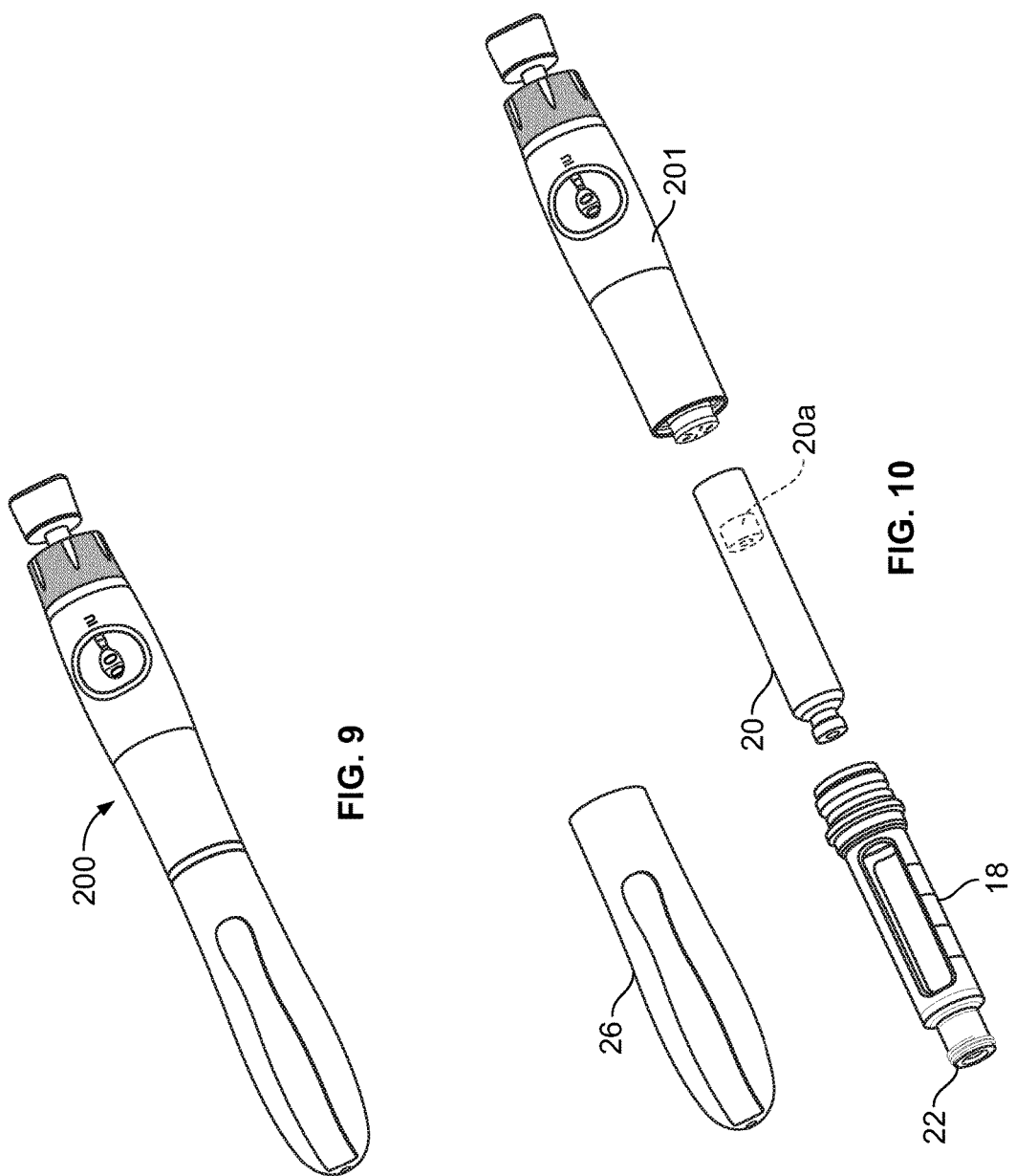

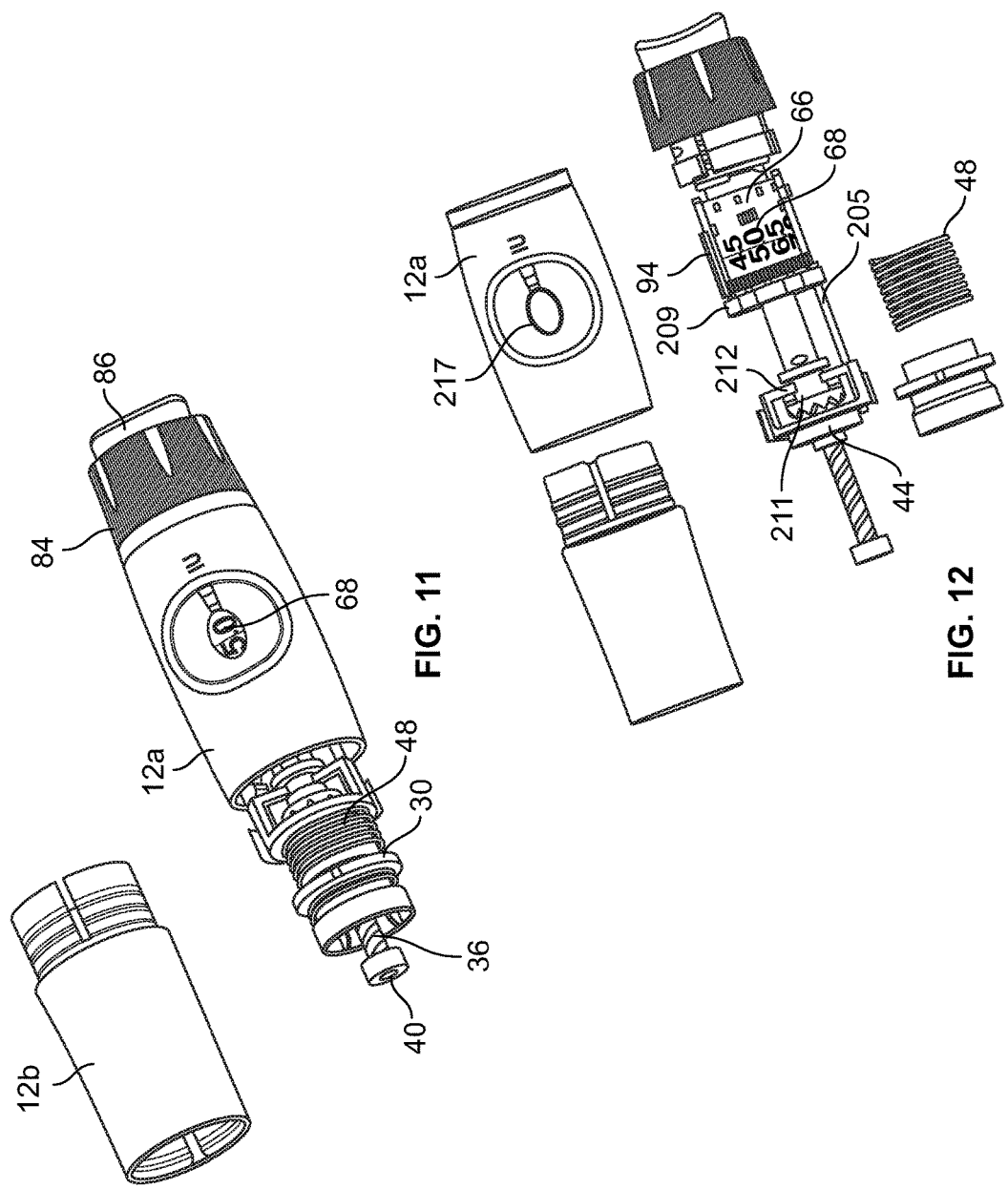

MEDICAMENT DELIVERY DEVICE

CROSS REFERENCE TO RELATED APPLICATIONS

The present application is a continuation-in-part of U.S. patent application Ser. No. 14/948,641, filed Nov. 23, 2015, which is a continuation of U.S. patent application Ser. No. 14/449,671, filed Aug. 1, 2014, which is a continuation of U.S. patent application Ser. No. 13/896,639, filed May 17, 2013, now U.S. Pat. No. 8,827,962, which is a continuation of U.S. patent application Ser. No. 13/203,040, filed Jan. 31, 2012, now U.S. Pat. No. 8,491,536, which is a U.S. National Phase Application pursuant to 35 U.S.C. § 371 of International Application No. PCT/US2010/060022 filed Dec. 13, 2010, which claims priority to Swedish Patent Application No. 0950958-9 filed on Dec. 15, 2009. The entire disclosure contents of these applications are herewith incorporated by reference into the present application.

TECHNICAL AREA

The present invention relates to a medicament delivery device comprising a dose setting function.

BACKGROUND

Medicament delivery devices such as injectors are sometimes provided with functions where a specific dose can be set by the user, which dose may be varied within a range.

Quite often this dose setting function is performed by turning a knob or wheel at the distal end of the device whereby it is moved in the distal direction. When performing a subsequent injection, the knob is pushed linearly in the proximal direction. One such injector is disclosed in the document U.S. Pat. No. 6,221,053 in which the distal dose knob of the injector is threaded out of a rod barrel tube as a dose is set. Thus the distance the knob is moved in the distal direction is directly related to the dose quantity to be delivered.

One drawback with that type of solution is that if larger doses are to be delivered the dose knob has to be moved quite a long distance in the distal direction, which means that it might be difficult for a user to push the dose knob in the proximal direction during injection.

SUMMARY

The aim of the present invention is to remedy the drawbacks of the state of the art medicament delivery devices and to provide a device by which it is possible to set a desired or required dose in a simple and intuitive way.

This aim is obtained by a medicament delivery device according to the features of the independent patent claim. Preferable embodiments of the invention are subject of the dependent patent claims.

Another aim of the present invention is to provide a locking assembly that reliably and repeatedly releases the dose button to an activated state when a user is ready to set a second dose and/or subsequent doses for injection. Failure to unlock the dose button and concurrently the lead screw, reliably each time a dose is to be set presents a potentially dangerous situation in that a user may not be able to set and administer needed subsequent doses of medicament from the drug delivery device. The drug delivery device must be reliably locked at the completion of injection procedure and then unlocked after each administered dose by dialing the dose setting knob to an initial start position or to a zero dose setting. Dialing to the initial start position causes the dose button and lead screw to pop out of the outer housing in a rearward distal direction.

Yet another aim of the present invention is to provide a dosing member, preferably both a primary dosing member and a secondary dosing member, that can be rotated during dose setting or dose cancellation such that the dosing member releasably locks or engages with an alignment member. The alignment member maintains the dosing member in a rotationally fixed position relative to the dosing window in the housing until the user purposely turns the dosing knob. The alignment prevents unwanted rotational drift of the dosing member.

According to a main aspect of the invention it is characterised by a medicament delivery device comprising a housing having opposite distal and proximal ends; a medicament container holder releasably connected to said housing; a medicament container arranged inside said medicament container holder; a threaded plunger rod arranged to pass through a first inner wall of the housing and arranged to act on a stopper in the medicament container; a lead screw member coaxially connected to the threaded plunger rod by co-acting first slidably-and-rotatably-locked means; wherein said device further comprises a nut coaxially connected to the threaded plunger rod by a treaded engagement between them, connected to the lead screw member by co-acting non-slidable-and-rotatable means, and connected to the housing by co-acting second slidably-and-rotatably-locked means; a primary dose member coaxially rotatable on the lead screw member when the device is in a non-activated state and connected to the lead screw member by co-acting third slidably-and-rotatably-locked means when the device is in an activated state; a locking member fixedly connected to the housing and releasably connected to the lead screw member by co-acting locking means; a first spring force means arranged between the first inner wall of the housing and the nut, wherein the first spring force means is in a pre-tensioned state when said locking means are engaged and the device is in the non-activated state; a secondary dose member rotatably connected to said primary dose member via a pinion gear; dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

According to a further aspect of the invention, said primary and said secondary dose members are provided with indicia.

According to another aspect of the invention, the locking means comprises a proximally pointing and radial flexible lever arranged on the locking member, an annular ledge on the circumferential surface of the lead crew member, and the circumferential inner surface of the secondary dose member; such that when the first spring force means is in a pre-tensioned state, the circumferential inner surface of the secondary dose member forces the flexible lever radial inwardly in contact with the ledge; and when the dose setting means are manually manipulated, the secondary dose member is rotated to a position wherein the flexible lever is radial outwardly flexed into a longitudinal groove on the inner circumferential surface of the secondary dose member.

According to yet a further aspect of the invention, the locking member comprises on its distal circumferential surface a distally pointing stop member, and wherein the secondary dose member comprises on its proximal circumferential surface a first and a second proximally pointing stop members arranged to interact with the stop member of the locking member.

According to yet another aspect of the invention, the non-slidable-and-rotatable means comprises ratchet arms and radial inwardly directed arms on the nut, grooves on the outer circumference of wheels on the proximal end of the lead screw member, and an annular groove between the wheels, wherein the ratchet arms cooperate with the grooves for giving an audible signal when the lead screw member is rotated; and wherein the radial inwardly directed arms cooperate with the annular groove such that the lead screw member and the nut are slidably locked and rotatable in relation to each other.

According to a further aspect of the invention, the first slidably-and-rotatably-locked means comprises radial inwardly directed ledges on the inner surface of the proximal end of the lead screw member, and longitudinally extending grooves on the plunger rod, wherein the grooves cooperate with the radial inwardly directed ledges such that the lead screw member and the plunger rod are rotationally locked and slidable in relation to each other.

According to another aspect of the invention, the second slidably-and-rotatably-locked means comprises grooves on the outer circumferential side surface of the nut, and longitudinal ribs on the inner surface of the housing, wherein the grooves cooperate with the longitudinal ribs such that the nut and the housing are rotationally locked and slidable in relation to each other.

According to yet a further aspect of the invention, the third slidably-and-rotatably-locked means comprises splines on the outer circumferential surface of the lead screw member, and corresponding splines arranged on the inner circumferential surface of the primary dose member, wherein the splines cooperate with corresponding splines such that the lead screw member and the primary dose member are rotationally locked and slidable in relation to each other.

According to yet another aspect of the invention, the dose setting means comprises a clutch plate provided with a first annular ratchet, a dose setting knob provided with a second annular ratchet, and a second spring force means arranged between a second inner wall of the housing and a proximal surface of the clutch plate, such that clutch plate is distally urged and the first and the second ratchet are abutting each other, and which dose setting knob protrudes through the distal end of the housing.

According to a further aspect of the invention, the fourth slidably-and-rotatably-locked means comprises longitudinally extending grooves on the outer circumferential surface of the primary dose member, and radial inwardly directed protrusions on the inner surface of the clutch plate, wherein the longitudinally extending grooves cooperate with radial inwardly directed protrusions such that the primary dose member and the clutch plate are rotationally locked and slidable in relation to each other.

According to another aspect of the invention, the plunger rod is arranged to be proximally moved a distance corresponding to a set dose to be delivered by manually manipulating the dose setting knob when the device is in the activated state.

Yet another aspect of the invention relates to reliably unlocking the dose injection button and lead screw when the dose setting mechanism transitions from a non-activated to an activated state. The dose setting mechanism includes a housing having a longitudinal axis, a lead screw positioned with the housing, and a locking assembly slidably fixed relative to the housing, the locking assembly is configured to transition from a locked position when the dose setting mechanism is in a non-activated state to an unlocked position when the dose setting mechanism is in an activated state, where the locking assembly has a pinion having an axis of rotation offset and parallel to the longitudinal axis; and a rotating plate operatively connected to the pinion. The rotation of the pinion can move the rotating plate from a first angular position corresponding to the non-activated state and to a second angular position corresponding to the activated state.

The rotating plate can also have a locking protrusion, which may be wedged shaped to assist in the engagement with a radially extending tab position on the nut. The tab may engage the locking protrusion during dose delivery to form a lock that prevents distal movement of the nut relative to the housing at the completion of the dose delivery. This occurs when the rotating plate is in the first angular position. The tab and the locking protrusion can become engaged when the rotating plate is in the first angular position and after a set dose has been delivered. Movement of the rotating plate from the first angular position to the second angular position results in disengagement of the tab and the locking protrusion. In some cases, the rotating plate and pinion are rotatably connected through cooperating gear teeth. Also, the primary dosing member can be rotatably connected with the rotating plate and pinion through cooperating gear teeth.

Yet in another aspect, the present invention can include a dose setting mechanism for a medicament delivery device that has a housing having a longitudinal axis, a primary dosing member, a secondary dosing member, a first pinion axially fixed relative to the housing and having an axis of rotation offset and parallel to the longitudinal axis; and a second pinion axially fixed relative to the housing. The second pinion can have an axis of rotation offset and parallel to the longitudinal axis and can be rotatably connected to the primary dosing member, but not rotatably connected to secondary dosing member. Rotation of the second pinion can move a rotating plate from a first angular position corresponding to the non-activated state of the dose setting mechanism to a second angular position corresponding to the activated state.

This rotation of the second pinion causes the rotating plate and disengagement of a tab, located on the nut, from the locking protrusion on the rotating plate, where a biasing force then moves the nut in the distal direction. The first pinion is preferably always engaged with secondary doing member through gear teeth, but is only engaged with the primary dosing member through a gear segment at a single radial position as the primary dosing member is rotated through 360 degrees.

In another particular advantageous embodiment of the dose setting mechanism, an alignment member can be operatively connected to one of the primary dosing member and the secondary dosing member, where the alignment member is rotationally fixed to the housing. In some cases, the alignment member is operatively connected to both the primary dosing member and the secondary dosing member. The alignment member can have a first indexing nib and a second indexing nib in axial alignment with each other and positioned parallel to the longitudinal axis. The indexing nibs preferably each project radially outward from separate flexible tabs. The primary and secondary dosing members can each have a plurality of indexing notches circumferentially positioned along inside surfaces of the primary and secondary dose members, where each indexing notch corresponds to one of a plurality of the indicia located on an outer surface of the dosing members.

In a preferred configuration of the dose setting mechanism, the rotation of the primary dosing member relative to the alignment member causes the first indexing nib to engage and fit into one of the plurality of indexing notches on the primary dosing member, where the engagement of the first indexing nib and the one of the plurality of indexing notches stabilizes the primary dosing member from rotational drift. Also, rotation of the secondary dosing member relative to the alignment member can cause the second indexing nib to engage and fit into one of the plurality of indexing notches on the secondary dosing member, where the engagement of the second indexing nib and the one of the plurality of indexing notches stabilizes the secondary dosing member from rotational drift.

There are a number of advantages with the present invention. Because the lead screw, e.g. the manually operating delivery means, protrudes outside the housing with the same length independent of the set dose quantity the manual dose delivery operation is the same independent of set dose, i.e. the lead screw member has always the same position when a dose has been set.

Compared to the state of the art medicament delivery devices, this solution is a great advantage for the user or patient who suffers of dexterity problems. Also when not in use, the lead screw member is inside the medicament delivery device and locked. The unlocking of the lead screw member is performed when said dose setting knob is turned to an initial position, preferably a zero-dose position.

These and other features and advantages will become apparent from the detailed description and from the accompanying drawings.

BRIEF DESCRIPTION OF THE FIGURES

In the detailed description reference will be made to the accompanying drawings in which FIGS. 1a,b are a cross-sectional view of a medicament delivery device according to the present invention;

FIG. 9 is a perspective view of a possible embodiment of the present invention;

FIG. 10 is a partially exploded view of the embodiment shown in FIG. 9;

FIG. 11 is a partially exploded perspective view of the dose setting mechanism of the embodiment shown in FIG. 9;

FIG. 12 is a further exploded perspective view of the dose setting mechanism of the embodiment shown in FIG. 9;

DETAILED DESCRIPTION

Figure 1A:
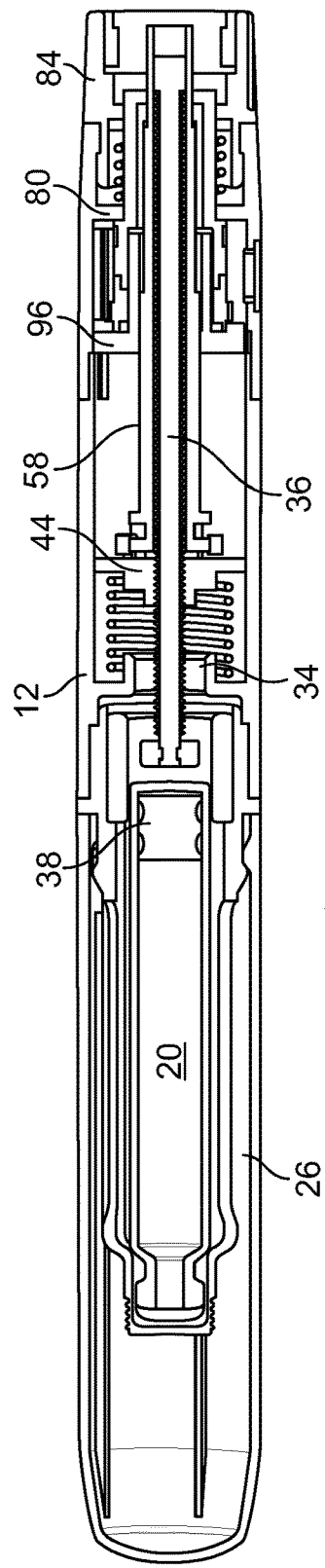

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

The medicament delivery device 10 according to the drawings comprises a generally elongated housing 12 having opposite distal and proximal ends. The elongated housing being e.g. divided in a proximal 12a and a distal part 12b. The proximal end of the housing is arranged with fastening means such as e.g. threads 14 on its inner surface, which fastening means cooperate with corresponding fastening means such as outwardly threads 16 on a distal end of a medicament container holder 18, providing a releasable connection. Inside the medicament container holder a medicament container 20 can be placed. The proximal end of the medicament container holder 18 is arranged with a threaded neck 22 for connection of a medicament delivery member such as an injection needle 24, a mouthpiece, a nozzle or the like, FIG. 2.

When received by a user, the medicament delivery device 10 is provided with a releasably attachable protective cap 26. At the distal end of the medicament container holder a sleeve-shaped container support 28 is inserted for holding and supporting the medicament container 20 when inserted, FIG. 2. At the proximal end of the housing a first inner wall 30 is arranged, which wall is provided with a central passage 32, FIG. 1b. The central passage is arranged with a distally directed tubular flange 34, FIG. 1a. A threaded plunger rod 36 extends in the longitudinal direction through the central passage 32 with a proximal end adjacent a stopper 38 inside said medicament container 20, FIG. 1a. The proximal end of the plunger rod 36 is further arranged with a plunger rod tip 40, FIG. 2.

The device further comprises a lead screw member 58 coaxially connected to the threaded plunger rod by co-acting first slidably-and-rotatably-locked means; and a nut 44 coaxially connected to the threaded plunger rod by a treaded engagement between them. The nut also being connected to the lead screw member by co-acting non-slidable-and-rotatable means, and to the housing by co-acting second slidably-and-rotatably-locked means.

Figure 2:
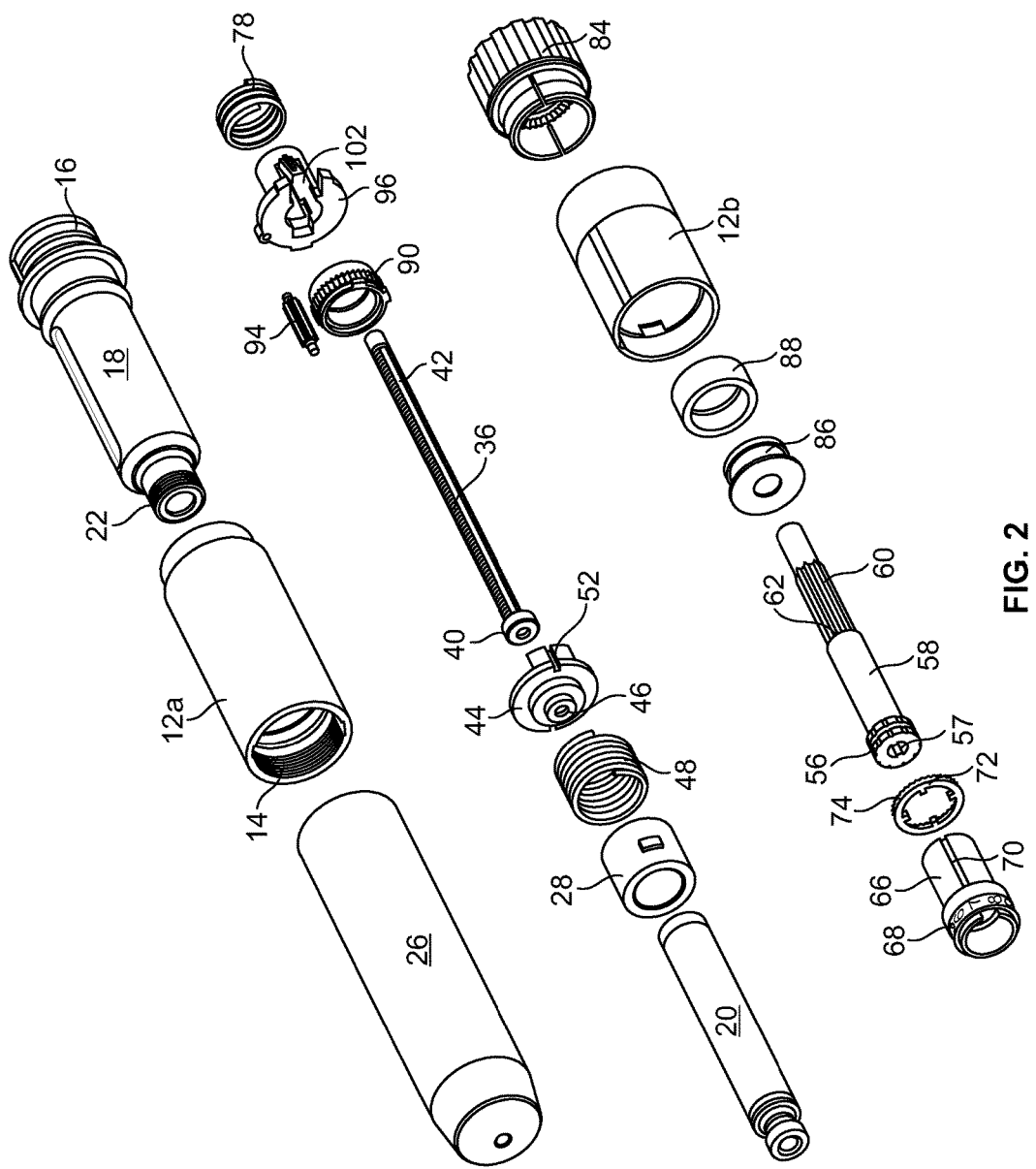
FIG. 2 is an exploded view of the medicament delivery device of FIGS. 1a,b.

The first slidably-and-rotatably-locked means comprises radial inwardly directed ledges 57 on the inner surface of the proximal end of the lead screw member, and longitudinally extending grooves 42 on the plunger rod, FIG. 2, wherein the grooves cooperate with the radial inwardly directed ledges 57 such that the lead screw member and the plunger rod are rotationally locked and slidable in relation to each other.

Figure 3:
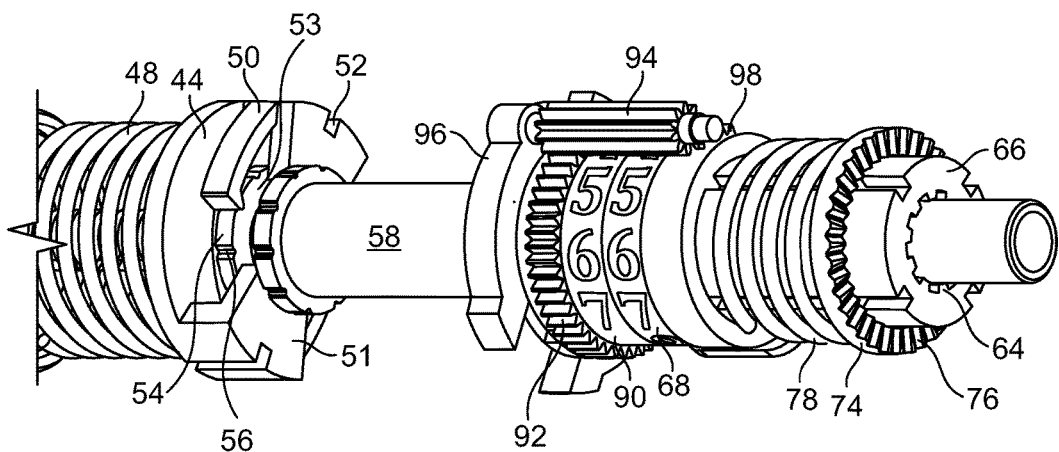
FIG. 3 is a detailed view of a dose-setting mechanism comprised in the present invention.

The non-slidable-and-rotatable means comprises ratchet arms 50 and radial inwardly directed arms 51 on the nut 44, grooves 56 on the outer circumference of wheels 54 on the proximal end of the lead screw member, and an annular groove 53 between the wheels 54, wherein the ratchet arms 50 cooperate with the grooves 56 for giving an audible signal when the lead screw member is rotated; and wherein the radial inwardly directed arms 51 cooperate with the annular groove 53 such that the lead screw member and the nut are slidably locked and rotatable in relation to each other, FIG. 3.

The second slidably-and-rotatably-locked means comprises grooves 52 on the outer circumferential side surface of the nut 44, FIG. 3, and longitudinal ribs on the inner surface of the housing (not shown), wherein the grooves cooperate with the longitudinal ribs such that the nut and the housing are rotationally locked and slidable in relation to each other.

The nut 44 comprises a threaded central passage 46 which cooperates with the threads of the plunger rod, FIG. 2, thereby forming the threaded engagement between them.

The device also comprises a primary dose member 66 coaxially rotatable on the lead screw member when the device is in a non-activated state and connected to the lead screw member by co-acting third slidably-and-rotatably-locked means when the device is in an activated state. The third slidably-and-rotatably-locked means comprises splines 60 on the outer circumferential surface of the lead screw member; and corresponding splines 64 arranged on the inner circumferential surface of the primary dose member, wherein the splines 60 cooperate with corresponding splines 64 such that the lead screw member and the primary dose member are rotationally locked and slidable in relation to each other, FIGS. 2 and 3.

The device further comprises:—a locking member 96 fixedly connected to the housing and releasably connected to the lead screw member by co-acting locking means;—a first spring force means 48 arranged between the first inner wall 30 of the housing and the nut, wherein the first spring force means is in a pre-tensioned state when said locking means are engaged and the device is in the non-activated state; and—a secondary dose member 90 rotatably connected to said primary dose member 66 via a pinion gear 94, FIG. 3.

The device also comprises dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

Figure 1B:
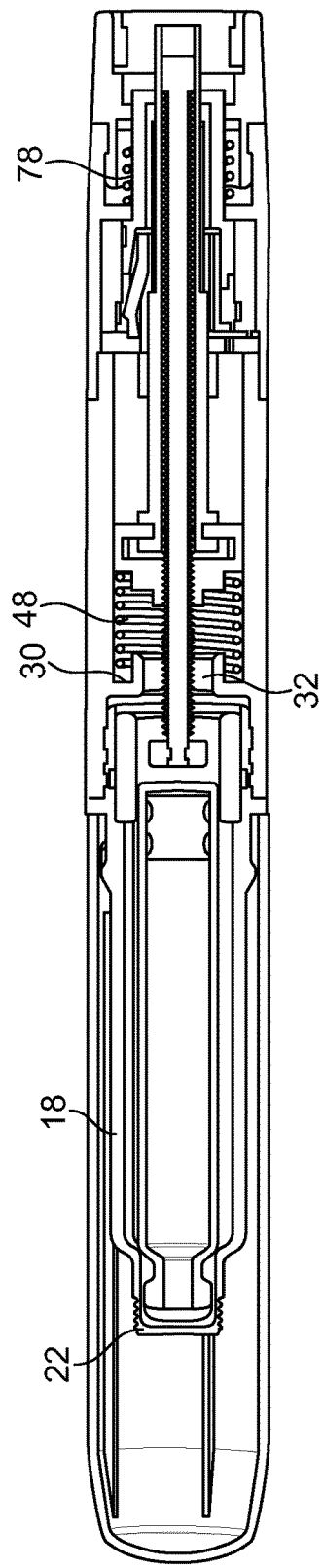
Figure 4:
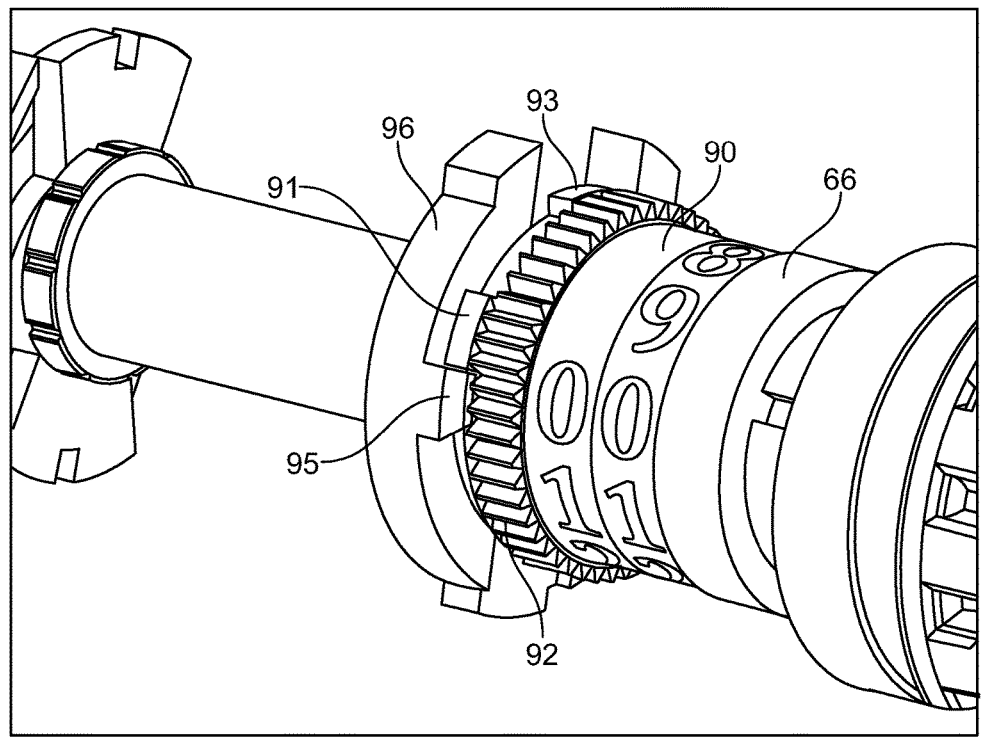
FIG. 4 is a further detailed view of the dose-setting mechanism comprised in the present invention.
Figure 5:
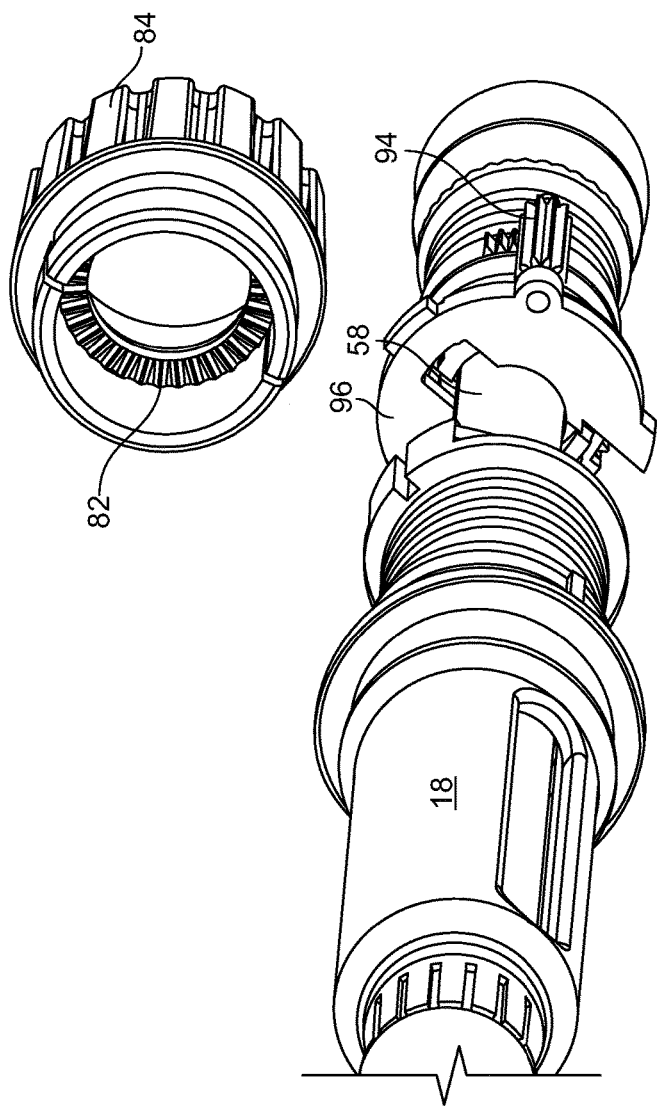
FIG. 5 is yet a further detailed view of the dose-setting mechanism comprised in the present invention.
Figure 6:
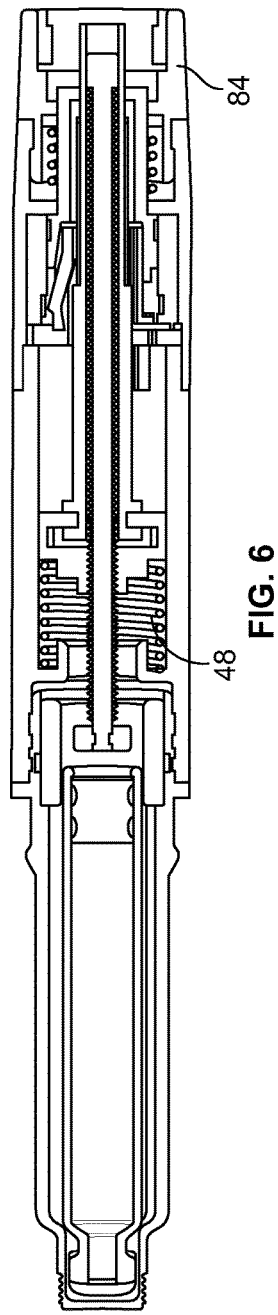
FIGS. 6, 7a, 7b, 8a, and 8b are cross-sectional view of different functional positions.

The dose setting means comprises a clutch plate 74 provided with a first annular ratchet 76, a dose setting knob 84 provided with a second annular ratchet 82, and a second spring force means 78 arranged between a second annular inner wall 80 of the housing and a proximal surface of the clutch plate, such that clutch plate is distally urged and the first and the second ratchet are abutting each other, and which dose setting knob protrudes through the distal end of the housing, FIGS. 1a and 4. The fourth slidably-and-rotatably-locked means comprises longitudinally extending grooves 70 on the outer circumferential surface of the primary dose member 66, and radial inwardly directed protrusions 72 on the inner surface of the clutch plate 74, wherein the longitudinally extending grooves 70 cooperate with radial inwardly directed protrusions 72 such that the primary dose member and the clutch plate are rotationally locked and slidable in relation to each other, FIGS. 2 and 3. The distal end of the lead screw member 58 protrudes through the dose setting knob 84, and is at its distal end arranged with a dose injection button 86, FIGS. 2 and 7b. Outside the dose injection button 86 a spin ring 88 is rotatably arranged, FIG. 2.

The locking means comprises:—a proximally pointing and radial flexible lever 102 arranged on the locking member,—an annular ledge 62 on the circumferential surface of the lead crew member, and—the circumferential inner surface of the secondary dose member, FIG. 2. The secondary dose member 90 is also arranged with teeth 92 arranged around its circumference, which teeth cooperate with teeth on the pinion gear 94, which is journalled in the housing as well as the locking member 96 via a locking lever bracket, FIG. 3. Further the primary dose member 66 is arranged with a gear segment 98, which also cooperate with the pinion gear 94, FIG. 3. A certain part of the lead screw member 58 is arranged with the splines 60 on its outer circumferential surface, FIG. 2; which splines have a lesser diameter than the proximal part of the lead screw member, thereby creating the annular ledge 62, FIG. 2. The locking member 96 also comprises on its distal circumferential surface a distally pointing stop member 95, and the secondary dose member 90 comprises on its proximal circumferential surface a first 91 and a second 93 proximally pointing stop member arranged to interact with the stop member of the locking member, FIG. 4.

The proximal part of the primary dose member 66 and the secondary dose member 90 are arranged with a circumferential band containing numbers or indicia 68 which are used to indicate dose size through a dose window on the housing, as will be explained below, FIG. 3.

The device is intended to function as follows. When delivered to the user, the device is in the non-activated state wherein a medicament container 20 has been inserted in the medicament container holder 18 in the proximal end of the device, FIG. 1, the first spring force means is in a pre-tensioned state and said locking means are engaged, wherein the circumferential inner surface of the secondary dose member 90 forces the flexible lever 102 radial inwardly in contact with the ledge 62.

When the device is to be used the protective cap 26 is removed and the dose setting means are manually manipulated for setting the device from the non-activated state to the activated state by rotating the dose setting knob 84 counter clockwise until activating indicia as e.g. two zeros are visible through the window of the housing. The rotation of the dose setting knob 84 causes the clutch plate 74 and thereby the primary dose member 66 to rotate due to the engagement between the co-acting fourth slidably-and-rotatably-locked means, and due to the connection between the first 76 and the second 82 ratchets. However, the lead screw member is not rotated since the third slidably-and-rotatably-locked means 60, 64 are not in engagement, i.e. the splines 60 on the outer circumferential surface of the lead screw member and the corresponding splines 64 arranged on the inner circumferential surface of the primary dose member 66 are not in engagement. The secondary dose member 90 also rotates due to the connection between the gear segment 98 of the primary dose member 66 and the teeth 92 of the secondary dose member 90 through the pinion gear 94. The rotation of the secondary dose member 90 is stopped when its second proximally pointing stop member 93 abuts the distally pointing stop member 95. This causes a longitudinal groove on the inner circumferential surface (not shown) of the secondary stop member to be aligned with the flexible lever 102 whereby the flexible lever is radial outwardly flexed into the groove and thereby moved out of contact with the ledge 62 of the lead screw member 58. This causes the lead screw member 58 to move a pre-determined distance in the distal direction due to the force of the spring 48 acting on the nut 44, which in turn is attached to the lead screw member 58. The splines 60 on the outer circumferential surface of the lead screw member and the corresponding splines 64 arranged on the inner circumferential surface of the primary dose member are then engaged to each other. Because of the movement of the nut 44, the plunger rod 36 is also moved. The distal end of the lead screw member 58 and its dose injection button 86 now protrude distally out of the housing said predetermined distance and independent of the size of the dose to be set.

Figure 7A:
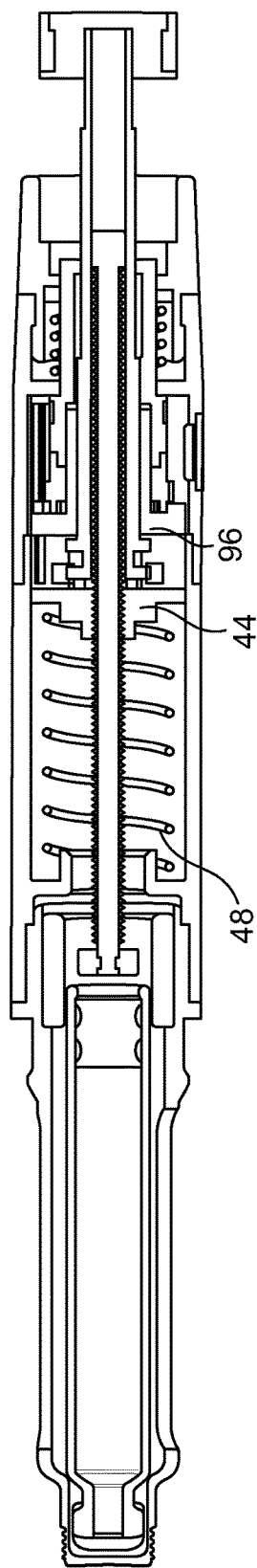
Figure 7B:
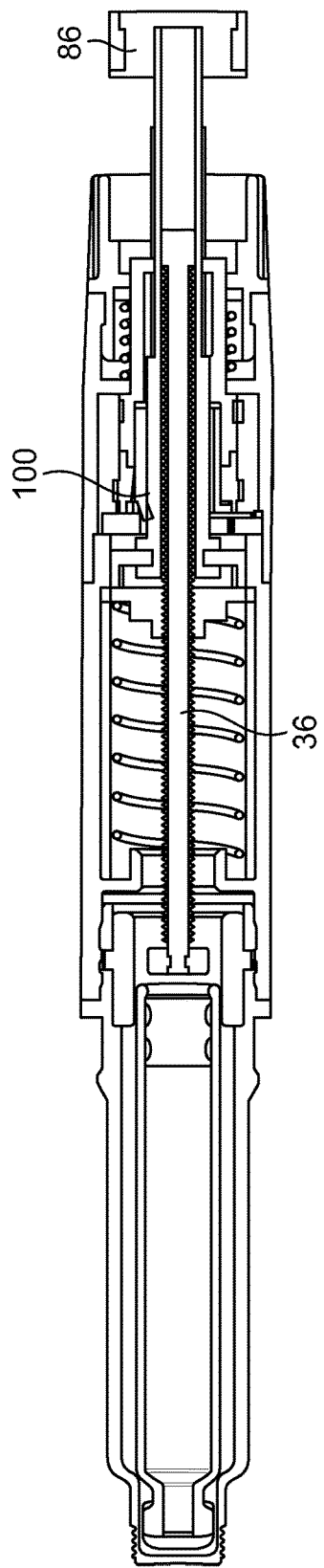

The device is now in the activated state and ready for setting a required dose of medicament, FIGS. 7a and 7b.

When setting a dose, the plunger rod is arranged to be proximally moved a distance corresponding to a set dose to be delivered by manually manipulating the dose setting knob. The dose setting knob 84 is rotated in the clockwise direction which also rotates the primary dose member 66 clockwise indicating the dose that is being dialled. At the same time the primary dose member 66 rotates the lead screw member 58 clockwise due to the engagement between the co-acting third slidably-and-rotatably-locked means 60, 64; and the lead screw rotates the plunger rod due to the engagement between the co-acting first slidably-and-rotatably-locked means, driving the plunger rod 36 through the nut 44 because of the threaded engagement between them, thereby moving the plunger rod 36 proximally. The secondary dose member 90 also rotates due to the connection between the gear segment 98 of the primary dose member 66 and the teeth 92 of the secondary dose member 90 through the pinion gear 94. The rotation of the secondary dose member 90 is stopped when its first proximally pointing stop member 91 abuts the distally pointing stop member 95, which indicates the maximum dose the device can deliver e.g. two indicia as e.g. a seven and a zero are visible through the dose window. In any case, the set dose is visible through the dose window of the housing. At this point the device is ready for an injection.

Moreover, if the user attempts to dial past the maximum dose the device can deliver or if the user attempts to dial pass the activating indicia, the connection between the first annular ratchet 76 and the second annular ratchet will function as a clutch.

Figure 8A:
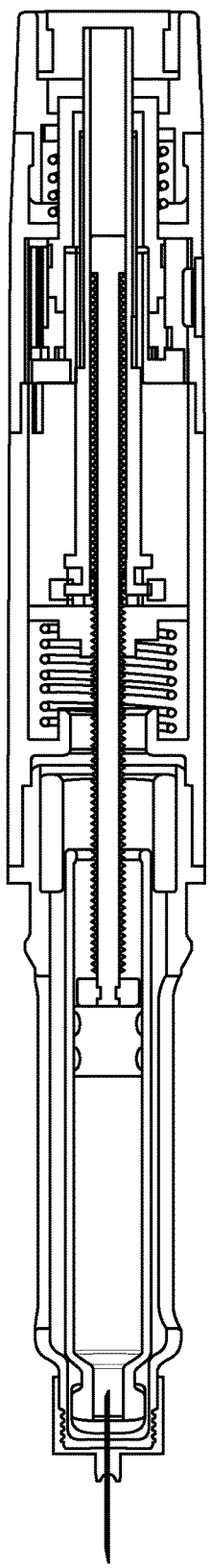
Figure 8B:
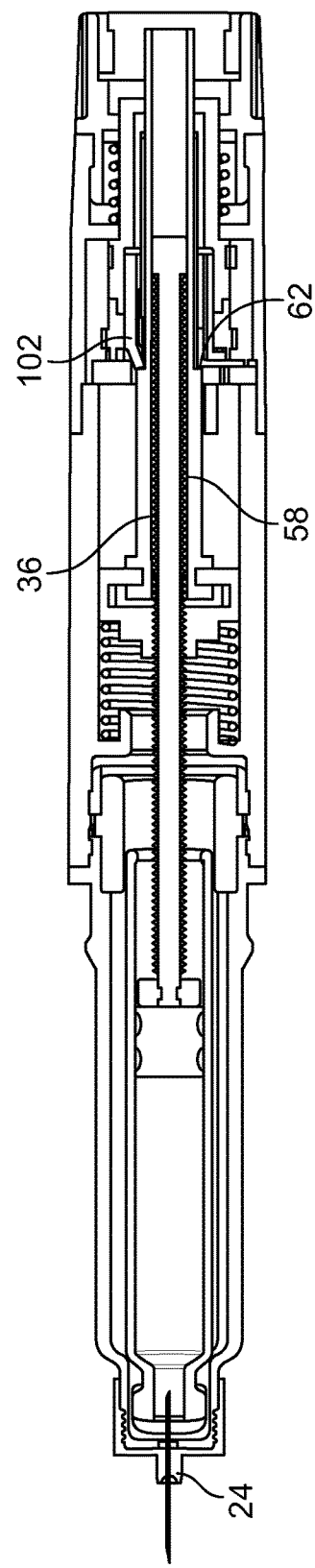

When the dose is set, a medicament delivery member 24 is attached to the proximal end of the device, such as e.g. an injection needle. It is however to be understood that other types of medicament delivery members may be used in order to deliver a dose of medicament. The medicament delivery member is then placed at the delivery site and the user presses the dose injection button 86 in the proximal direction the predetermined distance that the distal end of the lead screw member 58 and its dose injection button 86 protrudes distally out of the housing and which said predetermined distance is independent of the size of the dose to be delivered. This causes the lead screw member 58 to move in the proximal direction as well as the nut 44 and the plunger rod 36. This proximal movement of the plunger rod 36 causes it to act on the stopper 38 of the medicament container 20 whereby a dose of medicament is expelled through the medicament delivery member 24. When the lead screw member 58 has reached a certain distance inside the housing, the flexible lever 102 of the locking member is again moved in contact with the ledge 62 of the lead screw member 58, FIG. 8. The medicament delivery member may now be removed and discarded.

When a subsequent dose is to be performed, the above described procedure is performed and can be repeated until the medicament container is emptied.

Another embodiment of the invention is presented in FIGS. 9-16. This embodiment 200 differs slightly in structure and operation from that of the above-described embodiments in that in this version of the device a different locking assembly is used where nut 44 is modified to include a tab 44 that extends radially outward. (see FIG. 13). It also differs in that it employs an alignment member that prevents one or both of the primary and secondary dosing members 66, 90 from rotational drift after a dose has been set by the user rotating the dose setting knob 84. These two features could also be used in an embodiment where the device was configured to only allow a user to set one preset, pre-selected or pre-determined dose setting. For example, the device 200 could be manufactured such that a single fixed dose of 5 units or 10 units is preselected and the user would not be able to dial a dose greater than or less than the one single dose. In such an embodiment, only a single dosing member would be needed. In other words, the device does not have variable dose setting functionality, instead this type of device is referred to as a fixed dose device.

In one possible embodiment of the device 200 there is a dose setting mechanism 201 shown in FIG. 10 and in more detail in FIGS. 11-16. The distal part 12a of the elongated housing 12 contains a window 217 that allows a user to view and/or feel indicia 68 printed or otherwise located on the outer circumferential surfaces of the dosing members 66 and 90. As illustrated in the figures, numbers can be used to indicate a set dose. Alternatively, other symbols can be used to provide the user with a visual clue or prompt as to what direction to rotate dose setting knob 84 when the dose setting mechanism is in the activated state. The activated state is achieved when the user rotates the dose setting knob to the zero dose position, which as exemplified in FIG. 9 as a pair of "0" or any other desired indicia to indicate the starting position.

The dose setting mechanism 201 has a non-activated and an activated state. When the device 200 is in the non-activated state, the locking assembly is engaged. The locking assembly is comprised of at least the rotating plate 207, the locking pinion 205 (second pinion), tab 206, and locking protrusion 208. This is best illustrated in FIG. 14B where the tab 208 located on nut 44 is securely engaged on the proximal side of locking protrusion 208, which is fixedly positioned on an inner surface of rotating plate 207. The inner surface of the rotating plate also contains a set of gear teeth 219 that engage and rotatably cooperate with gear 218 located at the proximal end of second pinion 205. The distal end of the second pinion 205 also has a gear 216 circumferentially position on the outside surface of the second pinion. The second pinion 205 is preferably held by alignment member 209 by a through hole 209a that allows pinion 205 to rotate relative to the alignment member and to allow the alignment member to slide axially relative to the pinion 205. The through hole 209a is preferably configured with a snap opening to allow the pinion 205 to be inserted into the through hole from the side.

Biasing member 48, shown as a compression spring in FIGS. 11 & 12, exerts an axial force in the distal direction against the nut 44, lead screw 58, piston rod 36, primary and secondary dosing members 66, 90 and dose button 86. This axial biasing force is opposed by the engagement of the tab 206 with locking protrusion 208. In the non-activated state, the dose button 86 is pushed into the dosing knob 84 (see FIG. 14B) and the indicia showing in window is typically the last set dose, i.e., some combination of indicia 68 other than a pair of "0" or the initial start position. In order to change the device to the activated state, the user needs to rotate the dose knob 84 until the dosing members 66, 90 are returned to the initial start position as illustrated in FIG. 10.

FIG. 14A illustrates the dose setting mechanism in the activated state. As stated, this is achieved when the dosing members are rotated to the initial start position or zero dose position. As the user rotates the dosing knob 84 in a counter-clockwise direction, the primary dosing member 66 also rotates in the same direction. The multiple gear teeth portions 214 that are positioned circumferentially around the outside surface of the primary dosing member 66 engage the gear teeth on the first pinion 94. As each portion of gear teeth 214 rotates past and engages pinion gear teeth 94a, the pinion 94 is rotated. This rotation of pinion 94 causes simultaneous rotation of the secondary dosing member 90 because gear teeth 215 are always in engagement with cooperating gear teeth 94a on pinion 94. Once the primary dosing member is rotated to a point near the initial start position, i.e., immediately before a "0" is displayed in the window (see FIG. 15), the gear segment 213 on the primary dosing member engages with gear 216 at the distal end of the second pinion 205. This engagement causes the pinion 205 to rotate with the primary dosing member.

The rotation of the second pinion 205 also causes rotation of gear 218 located at the proximal end of pinion 205. Since gear teeth 218a are engaged and cooperate with gear teeth 219 of rotating plate 207 (see FIG. 16), the rotation of pinion 205 causes the rotating plate 207 to rotate along an inside surface 12b moving from one angular position relative to the housing to a second angular position. The inside surface 12b is defined between two hard stops 12c. As the rotating plate 207 is moved relative to housing 12a, the locking protrusion 208 is simultaneously rotated out of engagement with the tab 206 on nut 44, which is rotatably fixed relative to housing 12a through spline engagement 220a, 220b. Once the disengagement of the tab and the locking protrusion is complete, the axial force generated by biasing member 48 causes the nut 44, lead screw 58, piston rod 36, primary and secondary dosing members 66, 90 and dose button 86 to move axially in the distal direction (see FIG. 14A). This places the device in the active stated state where the dose button is moved distally outward (so-called "popped out") from the dose setting knob 84 and housing 12a as a result of the axial movement in the distal direction of lead screw 58. This in contrast to FIG. 14B where the dose setting mechanism 201 is in the non-activated state where spring 48 is compressed (pre-tensioned) by the forward or proximal movement of lead screw 58 during dose delivery.

Figure 13:
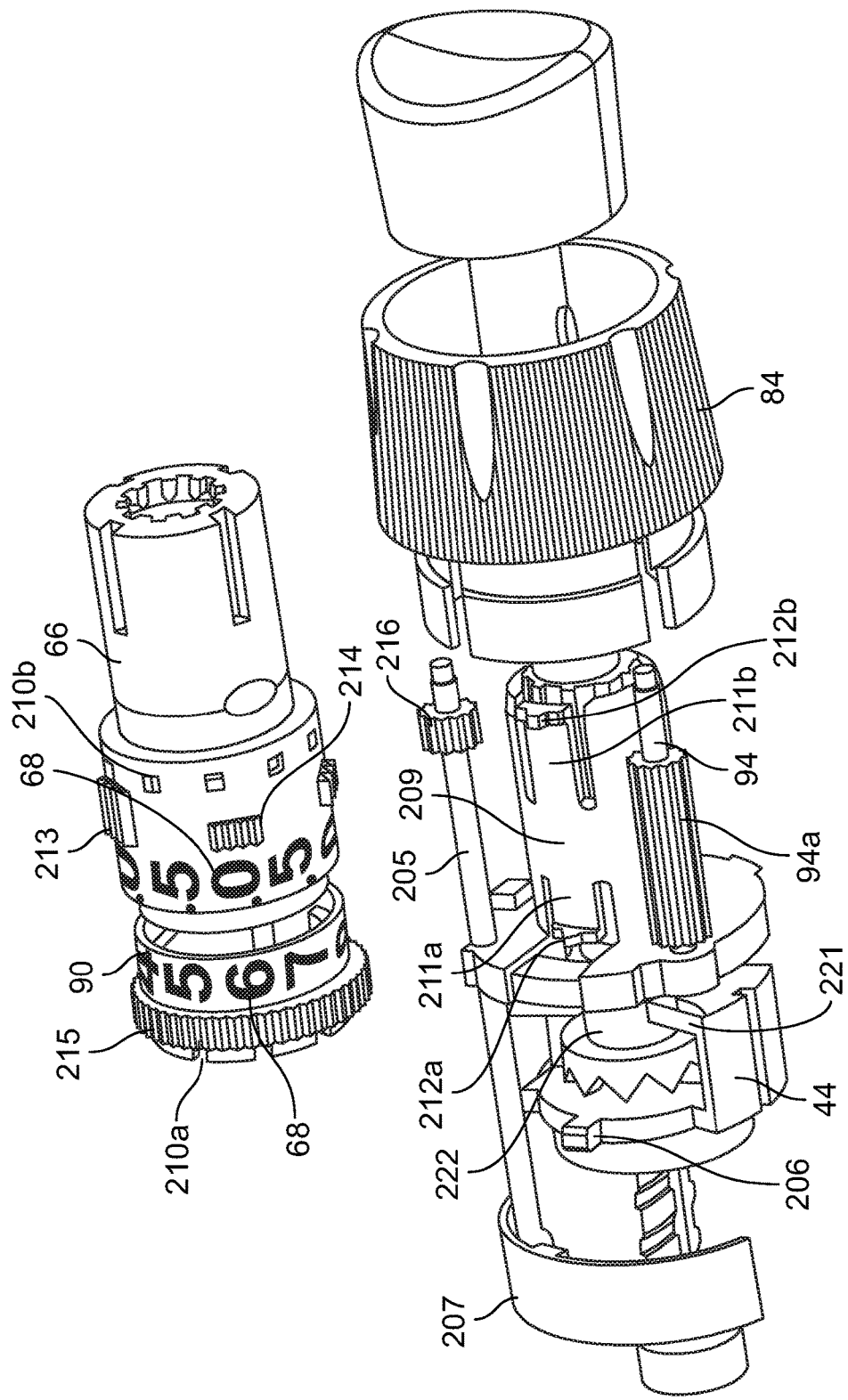
FIG. 13 is a exploded perspective view of the alignment member, locking assembly, lead screw and dose member of the embodiment shown in FIG. 9.
Figure 14:
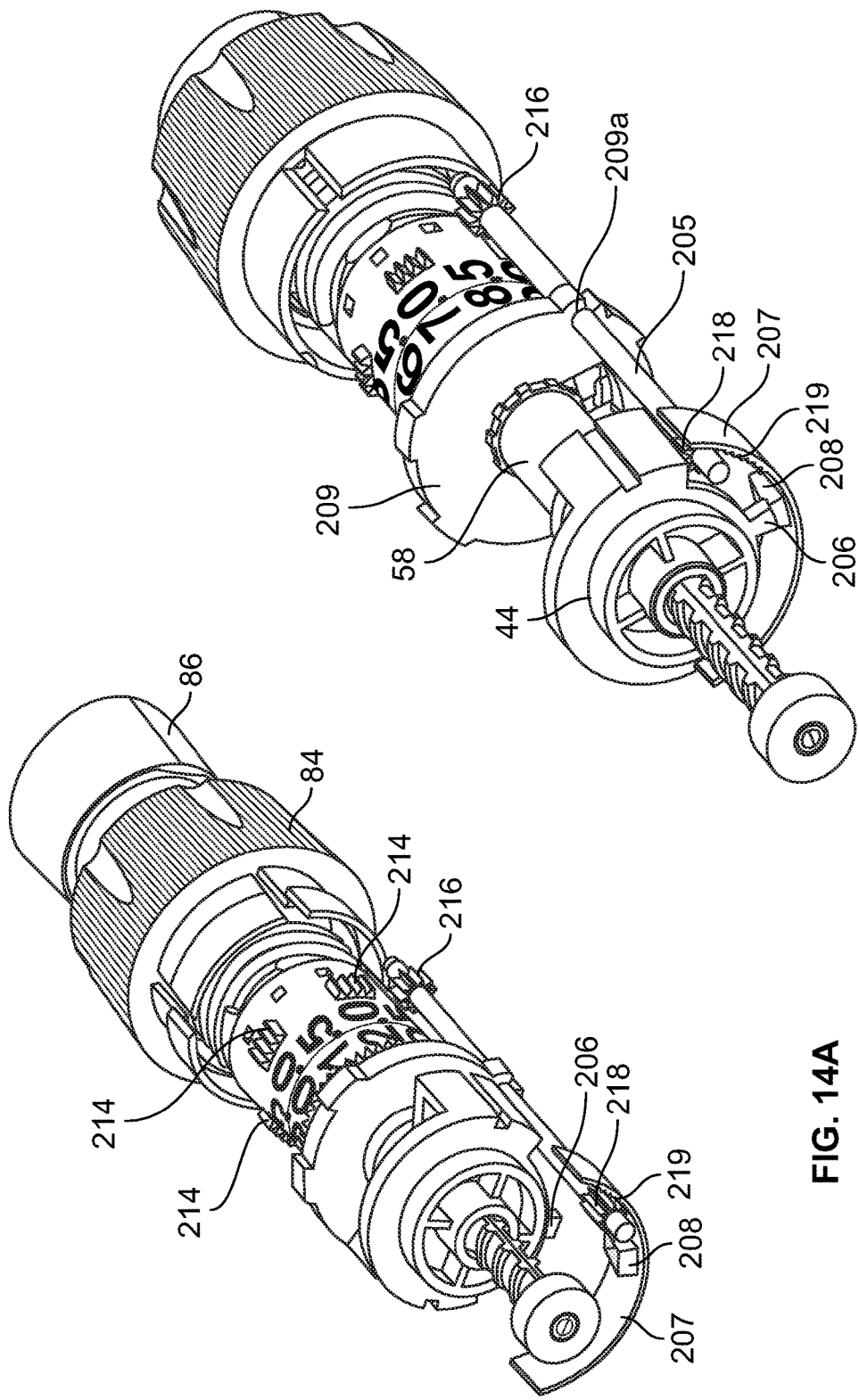
FIGS. 14A and 14B are close-up perspective views of the locking assembly when the dose setting mechanism in in an activated state and when in a non-activated state, respectively.

As mentioned, dose setting mechanism 201 can utilize an alignment member 209 (See FIG. 13) to prevent rotational drift of either or both of the primary and secondary dosing members. The particular embodiment shown in FIG. 13 illustrates an alignment member 209 that stabilizes both dosing members 66 and 90. Opposing flexible tabs 211a, 211b are incorporated into the outer circumferential surface of the alignment member 209. Each flexible tab has an indexing nib 212a, 212b that projects radially outward from the flexible tabs 211a, 211b. The indexing nibs are configured to cooperate and engagement with one of a plurality of indexing notches 210a, 210b located on the secondary and primary dosing members 90, 66, respectively. The engagement between the notches and the nib is releasable and functions as a detent. As the dosing members are rotated relative to the alignment member 209, which is rotationally fixed relative to housing 12a, the nibs releasably snap into and out of the indexing notches. When rotation is stopped, the engagement between a nib and a notch forms a connection this sufficient to prevent the dosing member from freely rotating relative to the housing, i.e., so called rotational drift. Preventing such rotational drift ensures the accuracy of the set dose that appears in window 217. The formed connection between the notch and the nib is easily overcome as the user rotates the dose knob 84 in either direction.

When two indexing nibs are present it is preferred to have them in axial alignment with each other and positioned parallel to the longitudinal axis. The indexing notches on the primary and secondary dosing members can be positioned circumferentially along inside surfaces of the primary and secondary dose members, where each individual indexing notch corresponds to one of a plurality of the indicia 68 located on an outer surface of the dosing members.

Figure 15:
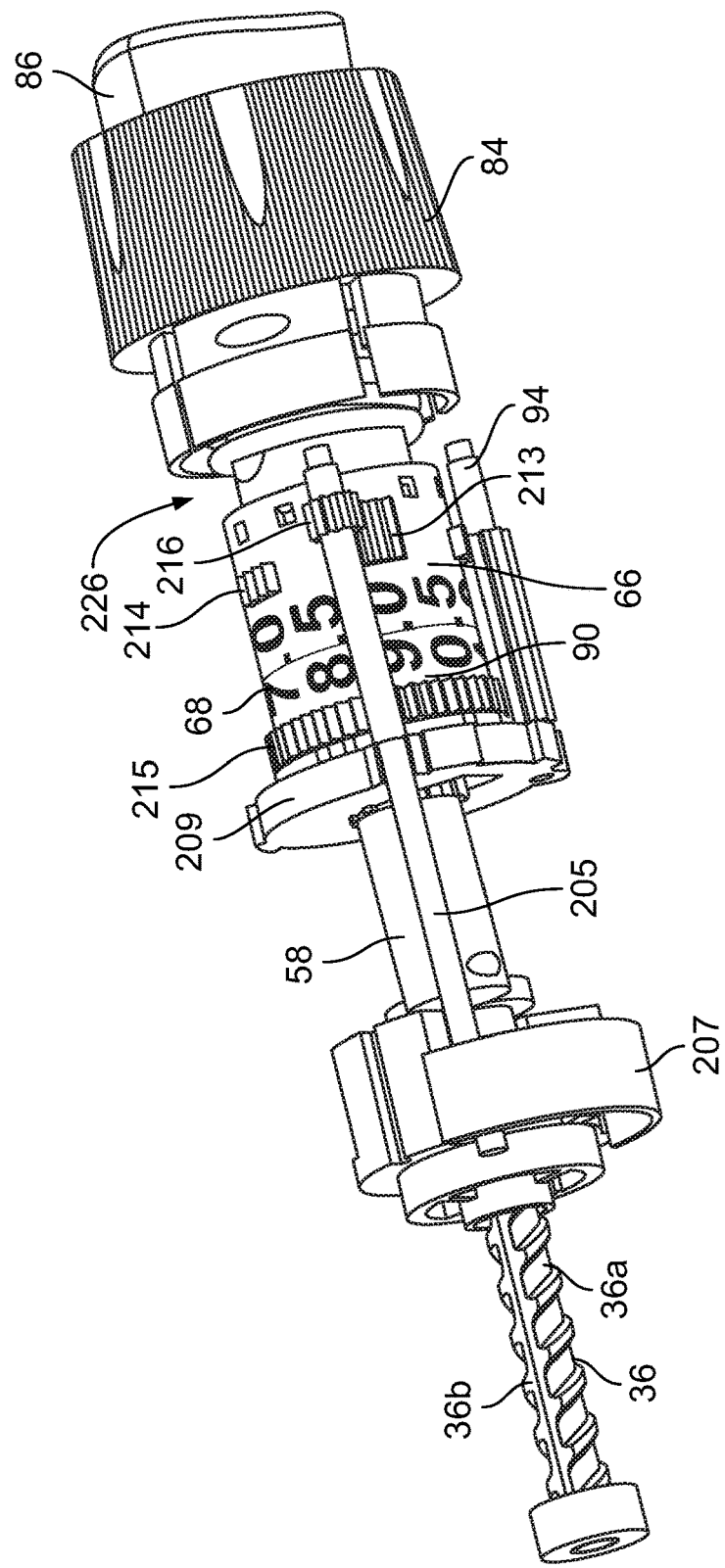
FIG. 15 is a close-up perspective view showing the two pinions of the embodiment shown in FIG. 9.

FIG. 15 shows the relationship of the first pinion 94 and the second pinion 205 relative to the dosing members 66, 90. This figure also shows the interaction of both gear teeth 215 and gear teeth 214 with the first pinion 94. Also shown, is the interaction of gear segment 213 with gear 216 on second pinion 205 when the device is in the activated state. The primary dosing member 66 is engaged and rotationally fixed the to the lead screw 58 such that rotation of the dose setting knob 84 causes the dose member to rotate as well as lead screw 58. FIG. 15 also illustrates the relationship of the plunger rod 36 to the lead screw 58. In the particular embodiment shown in FIG. 15, the plunger rod is shown with a non-circular cross-section having a pair of opposed flat surfaces 36b with threaded segments 36a between each flat portion 36b. A proximal through hole of lead screw 58 is configured to match the non-circular cross-sectional shape of plunger rod 36 such that the plunger rod is rotationally fixed to the lead screw 58, but can move or slide axially relative to the lead screw.

Figure 16:
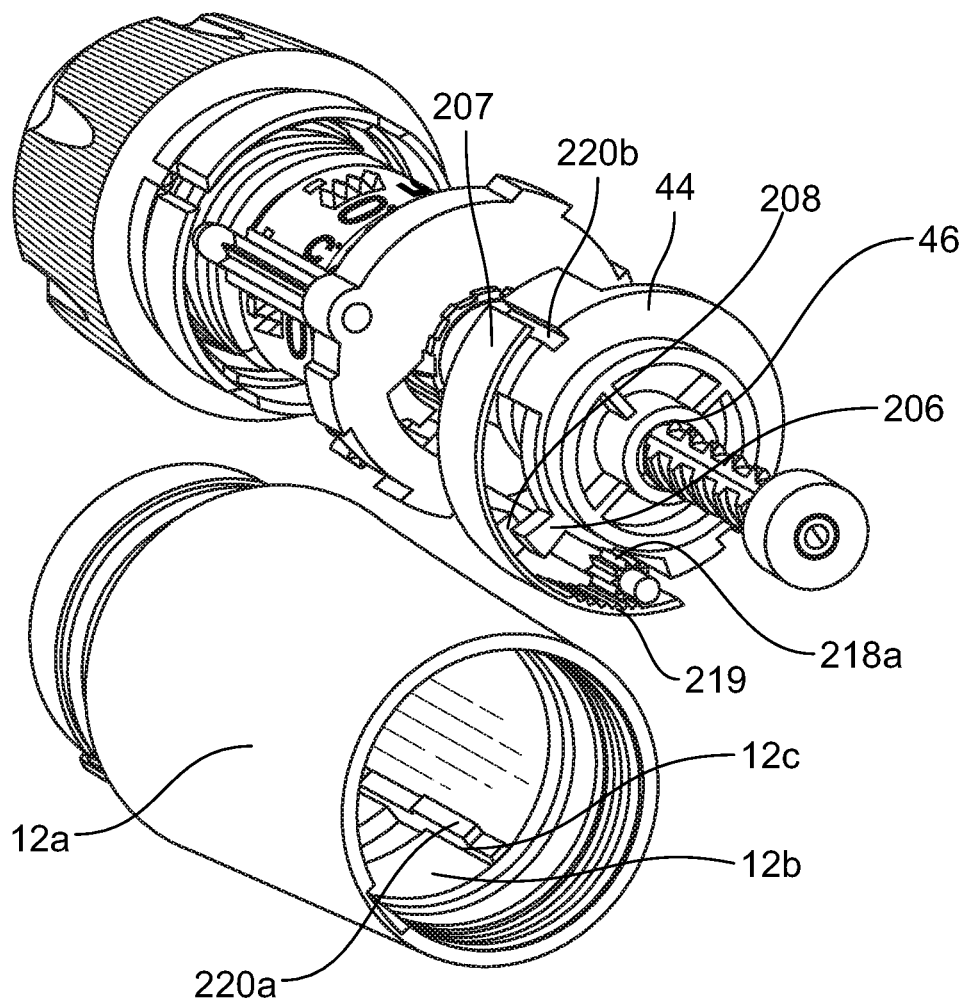
FIG. 16 is a close-up perspective and exploded alternative view of the locking assembly of the dose setting mechanism shown in FIG. 9.

The plunger rod 36 is threadedly engaged with nut 44 through threaded through hole 46 (see FIG. 16). Nut 44 is rotational fixed to the housing by the spline engagement 220a, 220b with the inside of the housing. This spline engagement allows the nut to slide axially relative to the housing. The nut 44 is fixed to the proximal end of lead screw 58 through the engagement of finger 221 in radial groove 222 at the proximal end of lead screw 58. This grove is sized with sufficient axial width such that the lead screw 58 and the distal face of the nut 44 can move axially relative to each other during dose setting. During dose setting the lead screw 58 is rotated relative to nut 44, which is rotationally fixed to the housing. The spring 48 exerts a biasing force in the proximal direction against the proximal face of the nut causing two opposed distally projecting ratchet teeth to engage complimentary proximally projecting ratchet teeth located at the proximal end of the lead screw. As the lead screw is rotated the ratchet teeth rotate relative to the stationary ratchet teeth causing the teeth to ride up and over teeth 221. This riding up and over motion moves the lead screw axially back and forth within groove. The nut is held in the groove by finger 221.

Figure 17:
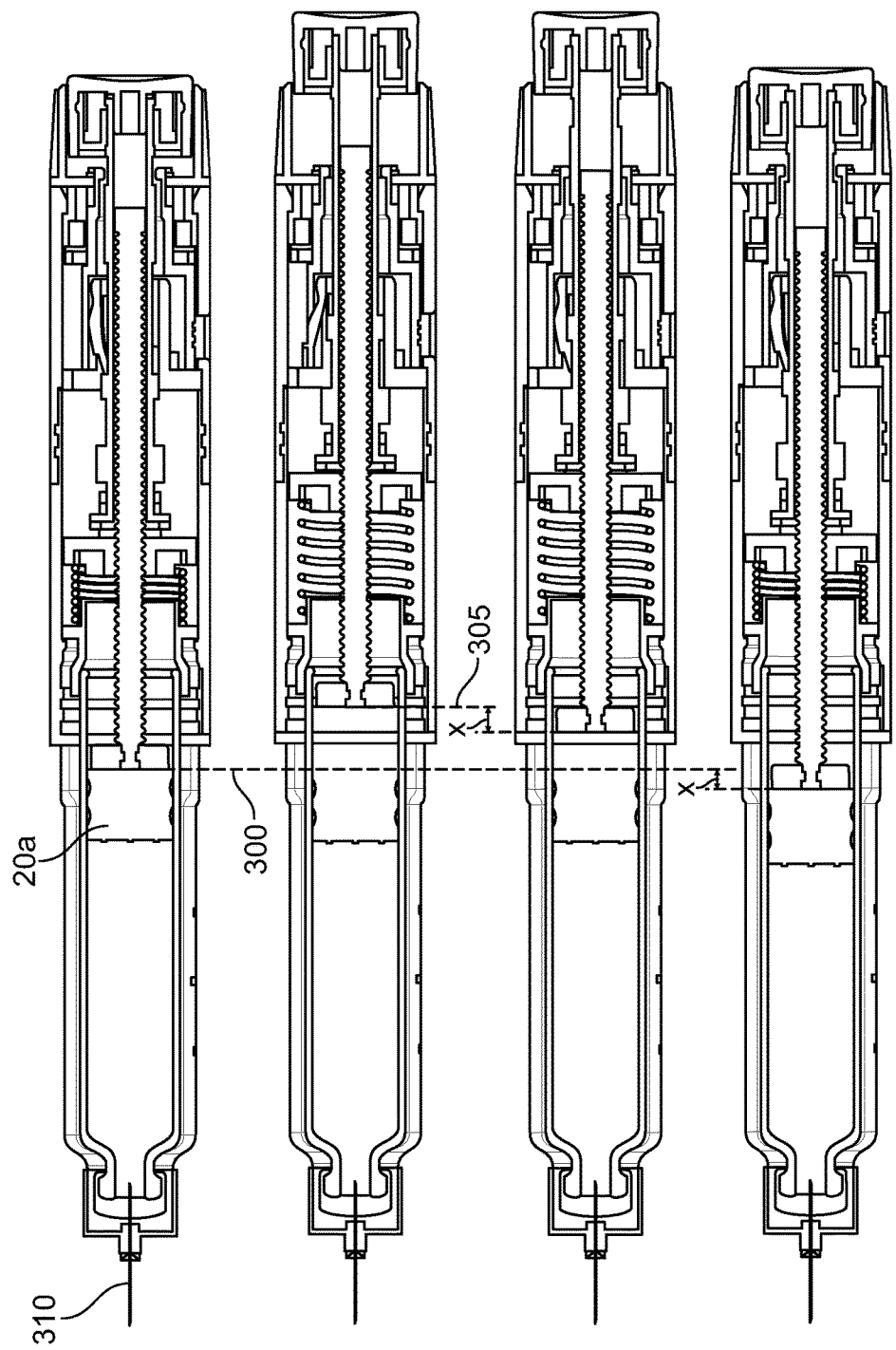
FIG. 17 are cross-sectional views of the sequence of operation of another embodiment of the present disclosure.

FIG. 17 illustrates the sequence of general operation of the various embodiments of the devices disclosed herein. The top figure shows the device in a non-activated state, for example, immediately after dose delivery. Here the dose button is pushed in (i.e., not "popped out") and the spring is in the pre-tensioned compressed state being held in this compressed state by the engagement of the flexible lever on the locking member locked with the ledge on the lead screw. The dose setting mechanism 201, as described above, would not have the locking member and instead would have the locking assembly where the tab on the nut is engaged with the locking protrusion on the rotating plate.

The next figure in FIG. 17 shows the device in the activated state when the dose setting knob is rotated to the zero dose or starting position, e.g., where the "00" is shown in the housing window. The transition from the non-activated to the activated state causes the lead screw, plunger rod and nut to all move distally by the biasing force exerted by the spring. The distance these three components move is always the same distance distally as indicated by the distance between lies 300 and 305. This moves the plunger rod off and away from cartridge piston 20a by the same distance. At this point, when the device is in the activated state, a dose can be set by rotating the dose setting knob. Since the plunger rod was moved distally off the cartridge piston when the zero dose position was obtained, the axial movement of plunger rod in the proximal direction does not move (or contact) the bung.

Setting a dose also rotates the primary dose member and possibly the secondary dosing member. The third figure in FIG. 17 represents the device with a dose set. Setting the dose caused the plunger rod to screw through the nut moving proximally a distance X. To deliver the set dose the user pushes the dose button proximally which pushes the lead screw, nut and plunge rod proximally as well. These three components move proximally and as the lead screw is pushed forward proximally, the flexible levers on the locking member that is axially fixed relative to the housing, flex over the ledge on the outside of the lead screw and causes the lead screw to be locked in the original most forward or proximal position, i.e., the non-activated state. As the lever re-engages the ledge on the lead screw, the spring is returned to the pre-tensioned state. Again, in the case of the embodiment of dose setting member 210, axial movement of the dose button in the proximal direction causes the tab to reengage the locking protrusion. As illustrated in the bottom figure of FIG. 17, the plunger rod moves an additional distance X representing and proportional to the dose set. This in turn moves the cartridge piston the same distance X and thus expels that amount of medicament from the proximal end of the cartridge through the injection needle 310.

It is to be understood that the embodiment described above and shown in the drawings is to be regarded only as a non-limiting example of the invention and that it may be modified in many ways within the scope of the patent claims.

The invention claimed is:

1. A dose setting mechanism for a medicament delivery device comprising:
   a housing having a longitudinal axis;
   a primary dosing member;
   a secondary dosing member;
   an alignment member operatively connected to one of the primary dosing member and the secondary dosing member, where the alignment member is rotationally fixed to the housing; and
   a pinion connected to the alignment member and having an axis of rotation offset and parallel to the longitudinal axis.

2. The dose setting mechanism of claim 1 where the primary dosing member and the secondary dosing member each contain a plurality of indicia.

3. The dose setting mechanism of claim 2 where the alignment member comprises a first indexing nib and a second indexing nib in axial alignment with each other and positioned parallel to the longitudinal axis, where the alignment member is operatively connected to both the primary dosing member and the secondary dosing member.

4. The dose setting mechanism of claim 3 where the first and second indexing nibs each project radially outward from separate flexible tabs.

5. The dose setting mechanism of claim 3 where the primary and secondary dosing members each further comprise a plurality of indexing notches circumferentially positioned along inside surfaces of the primary and secondary dose members, where each indexing notch corresponds to one of the plurality of indicia.

6. The dose setting mechanism of claim 5 where rotation of the primary dosing member relative to the alignment member causes the first indexing nib to engage and fit into one of the plurality of indexing notches on the primary dosing member, where the engagement of the first indexing nib and the one of the plurality of indexing notches stabilizes the primary dosing member from rotational drift.

7. The dose setting mechanism of claim 5 where rotation of the secondary dosing member relative to the alignment member causes the second indexing nib to engage and fit into one of the plurality of indexing notches on the secondary dosing member, where the engagement of the second indexing nib and the one of the plurality of indexing notches stabilizes the secondary dosing member from rotational drift.

8. The dose setting mechanism of claim 1 wherein the pinion is axially fixed relative to the housing.

9. The dose setting mechanism of claim 8 where the primary dosing member has a gear segment.

10. The dose setting mechanism of claim 9 where the secondary dosing member comprises an outside surface having gear teeth located circumferentially on the outside surface.

11. The dose setting mechanism of claim 10 where the pinion comprises an outer surface having a set of longitudinal teeth that cooperate and engage with the gear segment and the gear teeth on the secondary dosing member.

12. The dose setting mechanism of claim 11 where the pinion is always engaged with the gear teeth but is only engaged with the gear segment at a single radial position as the primary dosing member is rotated through 360 degrees.

13. The dose setting mechanism of claim 11 where the pinion engages the gear segment when the primary dosing member is rotated causing rotation of the pinion and simultaneous rotation of the secondary dosing member.

14. A dose setting mechanism for a medicament delivery device comprising:
   a housing having a longitudinal axis; a primary dosing member;
   a secondary dosing member;
   an alignment member operatively connected to both the primary dosing member and the secondary dosing member, where the alignment member is rotationally fixed to the housing;
   a first pinion rotatably positioned within the alignment member, where the first pinion is axially fixed relative to the housing and having an axis of rotation offset and parallel to the longitudinal axis; and a second pinion axially fixed relative to the housing and having an axis of rotation offset and parallel to the longitudinal axis wherein the second pinion is rotatably connected to the primary dosing member and is not rotatably connected to secondary dosing member.

15. The dose setting mechanism of claim 14 where the primary dosing member and the secondary dosing member each contain a plurality of indicia.

16. The dose setting mechanism of claim 15 where the alignment member comprises a first indexing nib and a second indexing nib in axial alignment with each other and positioned parallel to the longitudinal axis, where the first and second indexing nibs each project radially outward from separate flexible tabs.

17. The dose setting mechanism of claim 16 where the primary and secondary dosing members each further comprise a plurality of indexing notches circumferentially positioned along inside surfaces of the primary and secondary dosing members, where each indexing notch corresponds to one of the plurality of the indicia, wherein rotation of primary dosing member relative to the alignment member causes the first indexing nib to engage and fit into one of the plurality of indexing notches on the primary dosing member, where the engagement of the first indexing nib and the one of the plurality of indexing notches stabilizes the primary dosing member from rotational drift.

18. The dose setting mechanism of claim 14 further comprising a rotating plate operatively connected to the second pinion, where angular rotation of the rotating plate transitions the dose setting mechanism from a non-activated state and an activated state.

19. The dose setting mechanism of claim 18 where the rotating plate further comprises a locking protrusion, where the locking protrusion engages a tab radially extending from a nut, where the engagement prevents axial movement of the nut in a distal direction when the dose setting mechanism is in the non-activated state.

20. The dose setting mechanism of claim 19 where rotation of the second pinion rotates the rotating plate from a first angular position to a second angular position and causes disengagement of the tab and the locking protrusion allowing the dose setting mechanism to transition to the activated state.

* * * * *